United States Patent [19]
Aimoto et al.

[11] 3,935,307
[45] Jan. 27, 1976

[54] LIQUID OR PASTY DENTIFRICE AND PROCESS FOR PREPARING THE SAME

[75] Inventors: Kenji Aimoto, Toyonaka; Shigeru Hashimoto, Suita; Toyoaki Yoneda, Sakura, all of Japan

[73] Assignees: Teijin Limited, Osaka; Sunstor Dentrificy Co. Ltd., both of Japan

[22] Filed: May 30, 1974

[21] Appl. No.: 474,721

[30] Foreign Application Priority Data
June 5, 1973  Japan.............................. 48-62504

[52] U.S. Cl. ..................... 424/56; 424/49; 424/57
[51] Int. Cl.² ......................................... A61K 7/16
[58] Field of Search .............................. 424/49–58; 260/209 R

[56] References Cited
UNITED STATES PATENTS
3,506,757  4/1970  Salzmann............................. 424/52

FOREIGN PATENTS OR APPLICATIONS
2,114,066  10/1971  Germany

Primary Examiner—Richard L. Huff
Attorney, Agent, or Firm—Sherman & Shalloway

[57] ABSTRACT

A liquid or pasty dentifrice comprising, uniformly incorporated therein, a polysaccharide as a thickening and suspending agent, said polysaccharide having a number average molecular weight ($\overline{M}n$) of not less than 100,000 and the molecule of said polysaccharide containing D-glucose, D-mannose, D-galactose and succinic acid in the approximate molar ratio of 1 : 0.03 : 0.1 : 0.2. The polysaccharide is obtained by cultivating Alcaligenes faecalis var. myxogenes in a culture medium containing at least one member selected from the group consisting of lactic acid, pyruvic acid, succinic acid, fumaric acid, malic acid and esters thereof and saccharide.

6 Claims, 1 Drawing Figure

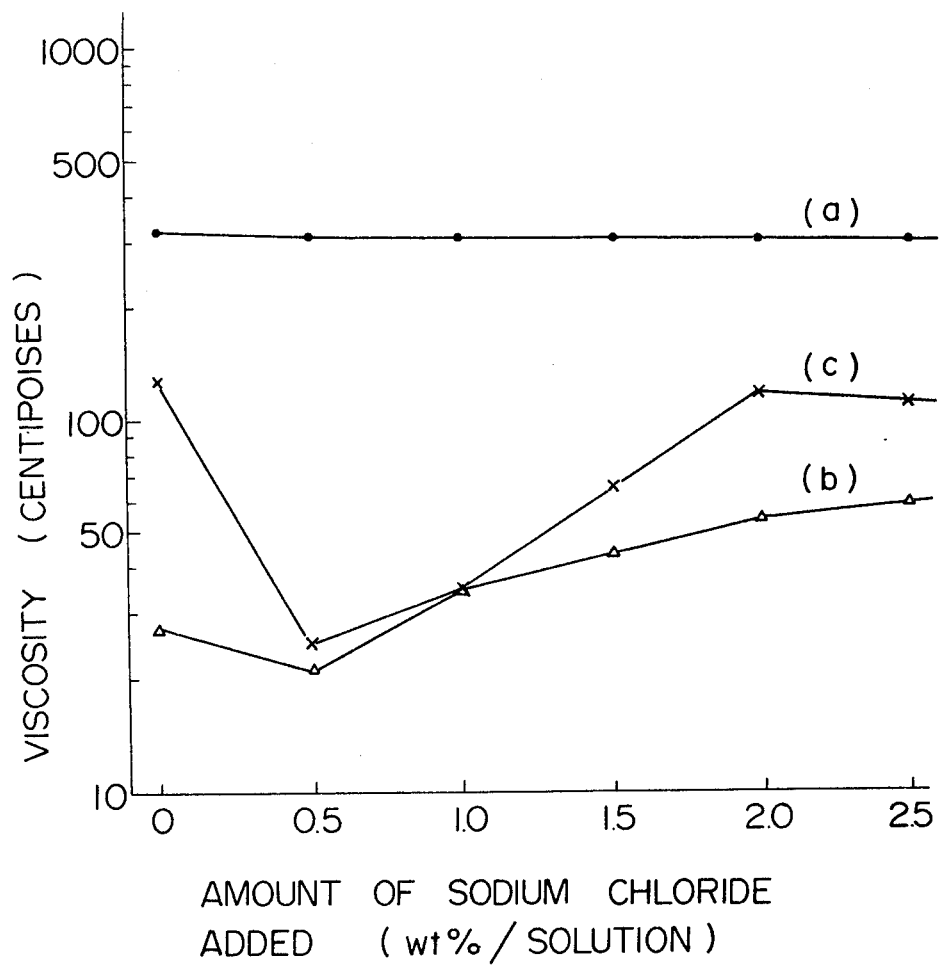

LIQUID OR PASTY DENTIFRICE AND PROCESS FOR PREPARING THE SAME

This invention relates to a liquid or pasty dentifrice having various properties which have been desired but have been unable to stand together in a single dentifrice, and to a process for preparing such a liquid or pasty dentifrice. More specifically, this invention relates to a liquid or pasty dentifrice comprising, uniformly incorporated therein, preferably in a proportion of 0.3 to 2 parts by weight per 100 parts by weight of the dentifrice, a thickening and suspending agent consisting of a polysaccharide having a number average molecular weight ($\overline{M}n$) of not less than 100,000, the molecule of the polysaccharide containing D-glucose, D-mannose, D-galactose and succinic acid in the approximate molar ratio of 1 : 0.03 : 0.1 : 0.2.

It has been known that by utilizing the ability of a xanthomonas hydrophilic colloid to form a stabilized suspension of an abrasive in a liquid dentifrice, the colloid is incorporated in the liquid dentifrice to provide a stable, homogeneous, pourable liquid dentifrice (U.S. Pat. No. 3,506,757 patented Apr. 14, 1970). It has also been known that by utilizing the ability of the xanthomonas hydrophilic colloid to improve the pourability of a pasty dentifrice from a container and its dispersibility in the mouth as compared with a conventional thickening and suspending agent such as Irish moss or a sodium salt of carboxymethyl cellulose, the colloid is incorporated into the pasty dentifrice to provide an improved pasty dentifrice (British Patent Application No. 4081/71 filed Feb. 5, 1971; corresponding to German OLS No. 2,204,670 laid open on Aug. 10, 1972).

The xanthomonas hydrophilic colloid described above is a polysaccharide reported, for example, in U.S. Pat. Nos. 3067038, 3391061, 3427226, 3516983, and 3519434. This polysaccharide can be prepared by cultivating Xanthomonas compestris in a medium containing a saccharide, and separating the resulting product from the culture medium. The above-cited U.S. Pat. No. 3,506,737 discloses the use of a polysaccharide the molecule of which contains mannose, glucose, potassium glucuronate and acetyl in the approximate molar ratio of 2 : 1 : 1 : 1 as the xanthomonas hydrophilic colloid to be incorporated in the liquid dentifrice. Furthermore, the German OLS No. 2,204,670 discloses the use of a partially acetylized polysaccharide, the molecule of which contains D-glucose, D-mannose and D-glucuric acid in the molar ratio of 2.8 : 3.0 : 2.0.

We have now found that a liquid or pasty dentifrice comprising another bacterial polysaccharide the molecule of which contains D-glucose, D-mannose, D-galactose and succinic acid in the approximate molar ratio of 1 : 0.03 : 0.1 : 0.2 has improved properties and superior resistance to putrefaction as compared with the conventional liquid or pasty dentifrice containing a xanthomonas hydrophilic colloid.

It has also been found that the dentifrice of this invention containing the above bacterial polysaccharide has a high solubility, a high water hold capacity, self-shape-maintaining properties (the property to retain a given shape as its own characteristic) and viscoelastic properties upon removal of an external pressure.

Furthermore, the above dentifrice of this invention has very good dispersibility and bubbling properties in the mouth, and disperse and retain the conventional dentifrice ingredients stably in the dentifrice, and does not lend itself to phase separation of the ingredients.

The polysaccharide used in this invention especially has superior solubility and salt resistance, and can be utilized for transparent dentifrices or as "salt-containing dentifrices" containing at least about 10% by weight of NaCl. It has been found that in such a case also, the polysaccharide does not give dentifrices having poor dispersibility in the mouth, unlike the case of carboxymethyl cellulose of a high degree of etherification which has been previously used as a thickening and suspending agent for dentifrices of this type.

Accordingly, an object of this invention is to provide an improved liquid or pasty dentifrice having superior properties and superior resistance to putrefaction compared with the conventional dentifrice containing a polysaccharide.

Another object of this invention is to provide a process for preparing such a dentifrice.

Many other objects of this invention along with its advantages will become more apparent from the following description.

The bacterial polysaccharide, the molecule of which contains D-glucose, D-mannose, D-galactose and succinic acid in the approximate molar ratio of 1:0.03:0.1:0.2, is known [Arch., Biochem. Biophy., 112, 65 (1965)], and can be obtained by cultivating a known microorganism Alcaligenes faecalis var. myxogenes (No. 10C3 strain: FERM-P. No. 2068; the Microorganism Research Institute, Agency of Industrial Science & Technology, Japan) in a culture medium containing at least one member selected from the group consisting of lactic acid, pyruvic acid, succinic acid, fumaric acid, malic acid and esters thereof and saccharide, and collecting the production formed in the medium. The physical and chemical properties of this polysaccharide and the method of its cultivation are described, for example, in Journal of Fermentation Technilogy 42 No. 10, p. 615 – 622, and Agricultual Biology and Chemistry 29 257 (1965).

There has previously been no attempt to incorporate this bacterial polysaccharide in a liquid or pasty dentifrice, and there has neither been any disclosure or suggestion that the resultant dentifrice has all of the above-mentioned improved properties. The following properties of the above known bacterial polysaccharide are known. Refined polysaccharide, which is called saccinoglucan is colorless, tasteless, and odorless, and it was soluble in water to give a clear solution, but insoluble in organic solvents such as alcohols, ethers, acetone, and chloroform. The pure polysaccharide is composed of D-glucose, D-mannose, D-galactose, and succinic acid in a molar ratio of 1:0.03:0.1:0.2, as determined from the results of column-chromatographic analysis of the acid hydrolyzate.

The polysaccharide, as used herein and the appended claims, denotes such a pure polysaccharide and a crude polysaccharide composed predominantly of such a pure polysaccharide. An aqueous solution of the polysaccharide is also known to have high viscosity comparable to that of gum guar, and the viscosity retains almost a constant value in the presence of acids or salts even when its concentration changes. The polysaccharide also has a high water hold capacity.

Nevertheless, the above high water hold capacity, self-shapemaintaining properties, stabilized dispersibility, the unique interaction with a salt or acid, and the resistance to putrefaction, etc. which are essential requirements for the present invention have not been known heretofore.

The bacterial polysaccharide utilized in this invention can be produced by methods known per se. For example, it can be prepared by cultivating Alcaligenes faecalis var. myxogenes in a culture medium containing at least one member selected from the group consisting of lactic acid, pyruvic acid, succinic acid, fumaric acid, malic acid and esters thereof, and saccharide, removing the cells and other solids from the culture liquid, adding a precipitant to the resulting liquid phase to precipitate crude polysaccharide, separating and collecting the precipitate, and if desired, purifying the precipitate.

The esters may, for example, be esters of monohydric alcohols having 1 to 10 carbon atoms, and of polyhydric alcohols having 2 to 12 carbon atoms. Specific examples of these alcohols are methanol, ethanol, propanol, isopropanol, butanol, t-butanol, hexanol, octanol, decyl alcohol, ethylene glycol, glycerin, sorbitol, and maltitol. Examples of the saccharide are glucose, mannose, galactose, lactose, maltose, glycerol, mannitol, sucrose, fructose and xylose.

The culture medium may further contain a nitrogen source and minerals.

Examples of the nitrogen source are peptone, urea, corn steep liquor, yeast extract, and ammonium sulfate.

Examples of the minerals are magnesium sulfate, monobasic potassium phosphate, calcium carbonate, and manganese sulfate.

The cultivation can be performed under aerobic conditions at a temperature of from about 22°C to about 39°C, preferably from about 27°C to about 35°C with the pH of the culture medium being maintained at from 6.0 to 8.0, preferably from 6.5 to 7.5. Usually, the cultivating time is about 40 hours to 5 days.

As the precipitant, there can be utilized an alcohol, an ether, acetone, chloroform, etc. Specific examples include methyl alcohol, isopropyl alcohol, acetone, chloroform, and an aqueous solution of a quaternary ammonium salt.

At this time, a subsidiary precipitant, for example, potassium chloride, can be used conjointly.

The crude polysaccharide obtained was dissolved in a suitable amount of water and precipitated by the precipitant described above to purify it. This dissolving-precipitating-separating cycle can be repeated a desired number of times. The polysaccharide obtained can be dried by vacuum drying or other means, and pulverized.

According to this invention, a liquid or pasty dentifrice can be provided by cultivating Alcaligenes faecalis var. myxogenes in a culture medium containing the member as described above, collecting the polysaccharide (meant to be both in the pure and crude forms) which has thus been produced in the culture medium and which has a number average molecular weight ($\overline{M}n$) of not less than 100,000, the molecule of said polysaccharide containing D-glucose, D-mannose, D-galactose and succinic acid in the approximate molar ratio of 1:0.03:0.1:0.2, and blending the resulting polysaccharide with a liquid or pasty dentifrice as a thickening and suspending agent in an amount of 0.3 to 2 parts by weight, preferably 0.5 to 1 parts by weight, per 100 parts by weight of the dentifrice.

The polysaccharide used in this invention has a number average molecular weight ($\overline{M}n$) of not less than 100,000, usually 100,000 to 500,000, preferably 150,000 to 450,000.

The number average molecular weight ($\overline{M}n$) is determined by measuring the viscosities of solutions of the above polysaccharide of the desalted type in various concentrations in a 1% aqueous solution of sodium hydroxide, obtaining the intrinsic viscosity $[\eta]$ by an extrapolating method, and substituting the intrinsic viscosity value for the Staudinger's equation below.

$$[\eta] = Km \cdot \overline{M}n^{\alpha}$$

wherein $Km = 3.08 \times 10^{-5}$, and $\alpha = 0.85$, which were used by Misaki et al. about a polysaccharide produced by *Bacillus Polymyxa var. lactoviscosus*.

The polysaccharide in the present invention need not altogether be of the desalted type, but may be in the form of an alkali metal salt such as a sodium or potassium salt, or an alkaline earth metal salt such as a calcium salt. Accordingly, the above polysaccharide used in this invention as a thickening and suspending agent includes not only a desalted type but also an alkali metal or alkaline earth metal salt type.

The dentifrice of this invention can further contain another known polysaccharide (B) having a number average molecular weight ($\overline{M}n$) of not less than 100,000, the molecule of said polysaccharide containing D-glucose, D-mannose, D-galactose and D-glucuronic acid in the approximate molar ratio of 3:3:1:2. Preferably, the polysaccharide (B) is used in an amount such that the total amount of the polysaccharide (B) and the polysaccharide (A) containing D-glucose, D-mannose, D-galactose and succinic acid in the approximate molar ratio of 1:0.03:0.1:0.2 does not exceed 2 parts by weight per part by weight of the dentifrice. Usually, the polysaccharide (B) is used in an amount of not more than 99% by weight, preferably not more than 80% by weight, more preferably not more than 70% by weight, based on the total amount of the polysaccharide (B) and the polysaccharide (A).

The bacterial polysaccharide (B), the molecule of which contains D-glucose, D-mannose, D-galactose, and D-glucuronic acid in the approximate molar ratio of 3:3:1:2, is known, and can be obtained by cultivating a known bacteria Bacillus polymyxa (No. 271 strain: FERM-P. No. 1824; the Microorganism Research Institute, Agency of Industrial Science & Technology, Japan) in a culture medium containing a saccharide, and collecting the polysaccharide produced in the medium. The physical and chemical properties of this polysaccharide and the method of its cultivation are described, for example, in Japanese Patent Publication No. 7600/67 and Die Angewandte Makromolekular Chemie., Band 6 (1969), pages 179 – 185.

The utilization of the above known polysaccharide (B) as a thickening and suspending agent for dentifrices is described in the copending application Ser. No. 435,184.

The dentifrice of this invention contains conventional well-known dentifrice ingredients such as humectants, detergents or surface active agents, flavoring materials, sweetening agents, abrasives, coloring materials, anticaries agents, fungicidal or bacteriocidal agents, or water. The use of the coloring materials, anti-caries agents, and fungicidal or bacteriocidal agents may be omitted. The amounts of these conventional dentifrice ingredients may be changed within the conventional ranges. Most commonly, in the case of a liquid dentifrice, a formulation consisting of 25 to 45% by weight of water, 20 to 35% by weight of abrasives, 20 to 35% by weight of humectants, 0.5 to 2% by weight of detergents or surface active agents, 0.3 to 2% by weight of the polysaccharide used in this invention, and the remainder being the other dentifrice ingredients can be utilized. In the case of a pasty dentifrice, the utilizable formulation consists of 25 to 35% by weight of water, 35 to 50% by weight of abrasives, 15 to 30% by weight of humectants, 0.5 to 2% by weight of detergents or surface active agents, 0.3 to 2% by weight of the polysaccharide used in this invention, and the remainder being the other dentifrice ingredients.

A part of the polysaccharide (A) used as a thickening and suspending agent can be replaced by a known thickening and suspending agent for dentifrice. The suitable amount of such a known thickening and suspending agent is not more than about 1.4 times the weight of the polysaccharide, preferably equal to the weight of the polysaccharide or less.

Examples of the conventional known thickening and suspending agents are carboxymethyl cellulose, its alkali metal salts, carrageenan, sodium alginate, hydroxyethyl cellulose, methyl cellulose tragacanth gum, locust beans gum, and tamarind seed-polysaccharide.

Examples of the humectants include glycerol, sorbitol, maltitol, glucose, propylene glycol, polyethylene glycol and sodium pyrrolidone carboxylate.

Examples of the abrasives are dicalcium phosphate dihydrate, calcium pyrophosphate, anhydrous dicalcium phosphate, insoluble sodium metaphosphate, hydrated alumina, calcium carbonate, magnesium carbonate, magnesium oxide, and finely powdered silica.

Examples of the detergents or surface active agents are sodium lauryl sulfate, sodium N-lauroyl sarcosinate, α-olefin sulfonate, sodium 2-hydroxyalkyl sulfate, sodium laurylether sulfate, sodium coconut monoglyceride sulfate, sodium coconut monoglyceride sulfonate, a sodium salt of a monoester of lauroylethanolamide sulfosuccinic acid, polyoxyethylene fatty acid esters such as polyoxyethylene sorbitan monolaurate, polyoxyethylene sorbitan monopalmitate, polyoxyethylene sorbitan monostearate, or polyoxyethylene stearate having a degree of polymerization of at least 25, and a polyoxyethylene polyoxypropylene block copolymer.

Examples of the flavoring materials are peppermint oil, spearmint oil, sassafras oil, clove oil, sage oil, Eucalyptus oil, marjoram oil, lemon oil, cinnamon oil, orange oil, and sodium methyl salicylate.

The sweetening agents may, for example, be sodium saccharate.

Examples of the coloring materials, anti-caries agents, and fungicidal or bacteriocidal agents are sodium fluoride, tin fluoride, hexachlorophene, and sodium monofluorophosphate.

An example of changes in apparent viscosity by the interaction between the polysaccharide used in this invention and salts is shown in FIG. 1 along with an example of changes in apparent viscosity of carboxymethyl cellulose, carrageenan and Xanthomonas hydrophilic colloid (conventional thickening and suspending agents) in the presence of salts.

In FIG. 1, the curve a shows the changes in the apparent viscosity (centi-poises) of a 0.5% aqueous solution of the polysaccharide (A) ($\overline{M}n = 400,000$) which has been measured at 25 C. using a Brookfield viscometer with No. 1 rotor at a speed of 30 rpm, with changes in the concentration (% by weight) of sodium chloride. Curves b and c shows similar changes in apparent viscosity with regard to carrageenan of κ-type (water-gel type) and λ-type (thickened type).

From FIG. 1, it is seen that in the present invention, a unique interaction between the polysaccharide and a salt occurs.

It can be seen from this fact that the polysaccharide (A) used in the present invention is suitable for use in the "salt-containing dentifrices".

The dentifrice of this invention has superior resistance to putrefaction as compared with the case of using Xanthomonas hydrophilic colloid.

A 1% aqueous solution of each of the polysaccharide (A) used in this invention and xanthane gum was blended with each of the antiseptics shown in Table 1 in the amount indicated. Each of the blends obtained was allowed to stand at about 40°C. for 2 weeks, and then the putrefying smell and bubbles formed as a result of putrefaction were observed. The results are shown in Table 1.

Table 1

| | Antiseptic | Amount of antiseptic (% by weight) | | | | | |
|---|---|---|---|---|---|---|---|
| | | 0 | 0.025 | 0.05 | 0.1 | 0.5 | 1 |
| Polysaccharide(A) of this invention | butyl p-oxybenzoate | − | − | − | − | − | − |
| | methyl p-oxybenzoate | − | − | − | − | − | − |
| | ethyl p-oxybenzoate | − | − | − | − | − | − |
| | potassium salt of sorbic acid | − | − | − | − | − | − |
| | hexachlorophene | − | − | − | − | − | − |
| Xanthane gum | butyl p-oxybenzoate | +++ | +++ | +++ | +++ | + | + |
| | methyl p-oxybenzoate | +++ | +++ | +++ | +++ | + | + |
| | ethyl p-oxybenzoate | +++ | +++ | +++ | +++ | + | + |
| | potassium salt of sorbic acid | +++ | +++ | +++ | +++ | +++ | +++ |
| | hexachlorophene | +++ | ++ | + | − | − | − |

The evaluations were made on the following scale.
+++ considerable putrefying smell, and evolution of much gas
++ putrefying smell, evolution of gas to a lesser extent than +++
+ putrefying smell and evolution of gas observed slightly
− neither putrefying smell nor evolution of gas observed.

These results demonstrate clearly that the polysaccharide used in this invention exhibits very good resistance to putrefaction.

The dentifrice of this invention has superior stability to heat, high solubility, high water hold capacity, stability with lapse of time and resistance to putrefaction, in addition to superior extrudability, dispersibility of solid dentifrice ingredients, shape retention after extrusion, smoothness of the surface of the extrudate, dispersibility in the mouth, break-off from the opening of the container at the time of extrusion foamability in the mouth, and flavor.

If a conventional thickening and suspending agent such as carboxymethyl cellulose is blended in the case of a lotion-like liquid dentifrice, the addition of a sufficient amount of a dentifrice abrasive results in the reduction of the viscosity of the resulting dentifrice. Accordingly, the amount of the thickening and suspending agent cannot but be reduced. As a result, the precipitation of a dentifrice abrasive is observed, and when the dentifrice thus obtained is poured onto a toothbrush, it cannot maintain its shape on the brush, but falls down among the brush hairs.

Furthermore, since the polysaccharide used in this invention has high solubility in water, the proportion of water can be reduced as compared with the case of using a conventional thickening and suspending agent such as carboxymethyl cellulose. Accordingly, it becomes easy to adjust the refractive index of a powder base such as silica gel of the dentifrice and that of the liquid component of the dentifrice, and the dentifrice is suitable as a transparent dentifrice.

Furthermore, the polysaccharide used in this invention has good salt resistance, it can be incorporated into the so-called "salt-containing dentifrice". In conjunction with the water-holding capacity, solubility and the non-dependence of the salt concentration on the viscosity, the good salt resistance leads to a "salt-containing dentifrice" having good dispersibility in the mouth.

The following Examples and Comparative Examples illustrate the liquid or pasty dentifrice of this invention. Unless otherwise specified, all parts are parts by weight and each polysaccharide (A) is obtained by cultivating Alcaligenes faecalis var. myxogenes (FERM-P. No. 2068 in the prescribed saccharide-containing culture medium. Polysaccharide (B) was obtained by cultivating Bacillus polymyxe (FERM-P. No. 1824).

Example 1 (liquid dentifrice)

| | |
|---|---|
| di-calcium phosphate dihydrate | 40.0 parts |
| Polysaccharide (A) | |
| (product in a glucose culture medium, average molecular weight about 300,000) | 1.0 part |
| Glycerol | 15.0 parts |
| Sorbitol | 13.0 parts |
| Water | 26.36 parts |
| Sodium laurylsulfate | 1.5 parts |
| Sodium saccharate | 0.1 part |
| Flavor | 1.0 part |
| Fungicide | 0.04 part |

The above polysaccharide A, fungicide and sodium saccharate were pre-mixed, and with stirring, glycerol was gradually added, followed by addition of water and sorbitol. By thorough mixing, the mixture became viscous. Di-calcium phosphate dihydrate was added to this mixture with stirring, and thoroughly dispersed. The flavor and sodium laurylsulfate were then added, and the mixture was stirrred in vacuo to form a uniform composition as a liquid dentifrice.

Example 2(liquid dentrifice)

| | |
|---|---|
| di-calcium phosphate dihydrate | 40 parts |
| Polysaccharide (A) | |
| (product in a malic acid culture medium, average molecular weight about 150,000) | 0.5 parts |
| Polysaccharide (B) | |
| (product in a succrose culture medium, average molecular weight about 500,000) | 0.5 parts |
| Glycerol | 15.0 parts |
| Sorbitol | 15.0 parts |
| Water | 26.36 parts |
| Sodium laurylsulfate | 1.5 parts |
| Sodium saccharate | 0.1 part |
| Flavor | 1.0 part |
| Fungicide | 0.04 part |

In accordance with the above formulation, a liquid dentifrice was prepared in the same way as in Example 1.

Example 3 (liquid dentifrice)

| | |
|---|---|
| di-calcium phosphate dihydrate | 40.0 parts |
| Polysaccharide (A) | |
| (the product in a succrose culture medium, average molecular weight about 300,000) | 0.5 part |
| Carboxymethyl cellulose | |
| (degree of etherification 0.7 – 0.8, degree of polymerization about 200) | 0.5 part |
| Glycerol | 15.0 parts |
| Sorbitol | 15.0 parts |
| Water | 26.36 parts |
| Sodium laurylsulfate | 1.5 parts |
| Sodium saccharate | 0.1 part |
| Flavor | 1.0 part |
| Fungicide | 0.04 part |

In accordance with the above formulation, a liquid dentifrice was prepared in the same way as in Example 1.

Example 4 (liquid dentifrice)

| | |
|---|---|
| di-calcium phosphate dihydrate | 30 parts |
| Polysaccharide (A) | |
| (product in a glucose culture medium, average molecular weight about 300,000) | 0.5 parts |
| Polysaccharide (B) | |
| (product in a glucose culture medium, average molecular weight about 500,000) | 0.5 parts |
| Glycerol | 30.0 parts |
| Water | 36.36 parts |
| Sodium laurylsulfate | 1.5 parts |
| Sodium saccharate | 0.1 part |
| Flavor | 1.0 part |
| Fungicide | 0.04 part |

In accordance with the above formulation, a liquid dentifrice was prepared in the same way as in Example 1.

Example 5 (liquid dentifrice)

| | |
|---|---|
| di-calcium phosphate dihydrate | 30.0 parts |
| Polysaccharide (A) | |
| (the product in a succinic culture medium, average molecular weight about 200,000) | 0.7 part |
| Carboxymethyl cellulose (The same one as Ex. 3) | 0.3 part |
| Glycerol | 30.0 parts |
| Water | 36.36 parts |
| Sodium laurylsulfate | 1.5 parts |
| Sodium saccharate | 0.1 part |
| Flavor | 1.0 part |
| Fungicide | 0.04 part |

In accordance with the above formulation, a liquid dentifrice was prepared in the same way as in Example 1.

Example 6 (pasty dentifrice)

| | |
|---|---|
| di-calcium phosphate dihydrate | 45.0 parts |
| Polysaccharide (A) (the product in a glucose culture medium, average molecular weight about 300,000) | 1.0 part |
| Glycerol | 10.0 parts |
| Sorbitol | 10.0 parts |
| Water | 30.86 parts |
| Sodium laurylsulfate | 1.5 parts |
| Sodium saccharate | 0.1 part |
| Flavor | 1.0 part |
| Fungicide | 0.04 part |

In accordance with the above formulation, a pasty dentifrice was prepared in the same way as Example 1.

For comparison, a pasty dentifrice (Comparative Example 1) was prepared in the same way except that Xanthomonas hydrophilic colloid was used instead of the polysaccharide in the above formulation, and a pasty dentifrice (Comparative Example 2) was also prepared in the same way except that carageenan was used instead of the polysaccharide in the above formulation.

The resistance to putrefaction of the pasty dentifrice obtained in Comparative Example 1 was compared with that of the dentifrice obtained in Example 6. Specifically, each of the pasty dentifrices were packed in a tube, and the changes with the passage of time in an atmosphere at about 40°C. were observed. It was found that the dentifrice of this invention did not give off bad smell nor evolve gas even after a lapse of 3 months, whereas the dentifrice of Comparative Example 1 gave off bad smell after a lapse of 2 weeks.

The syneresis of the dentifrice of Comparative Example 2 was compared with that of the dentifrice of Example 1. Each of the dentifrices extruded onto a sheet of white paper to a length of 5 cm. They were left to stand at 50°C. for the period described in Table 2, and then, the water separating phenomenon was observed. The results are shown in Table 2.

Table 2

| Pasty dentifrice | Time that elapsed (months) | | |
|---|---|---|---|
| | 1 | 2 | 3 |
| Example 1 | − | − | − |
| Comparative Example 2 | ± | + | ++ |

The symbols in the table represent the following evaluations.
− : no abnormality
± : the surface brightens slightly, and a slight syneresis can be observed.
+ : syneresis can be clearly observed
++: syneresis occurs to an extent that the dentifrice becomes useless The pasty dentifrice using carrageenan settled well, and had a good texture. On the other hand, however, it developed a syneresis phenomenon as is clearly seen from the results shown in Table 2, and this indicated that this pasty dentifrice has poor durability to storage for prolonged periods of time. In contrast, the pasty dentifrice of this invention is stable to storage for long periods of time, and does not exhibit any syneresis phenomenone, and has very good water-holding capacity.

Example 7 (pasty dentifrice)

| | |
|---|---|
| di-calcium phosphate dihydrate | 45.0 parts |
| Polysaccharide (A) (the product in a fumaric acid ester culture medium, average molecular weight about 100,000) | 0.5 part |
| Carboxymethyl cellulose (The same one as Example 3) | 0.5 part |
| Glycerol | 10.0 parts |
| Sorbitol | 10.0 parts |
| Water | 30.86 parts |
| Sodium laurylsulfate | 1.5 parts |
| Sodium saccharate | 0.1 part |
| Flavor | 1.0 part |
| Fungicide | 0.04 part |

In accordance with the above formulation, a pasty dentifrice was prepared in the same way as in Example 1.

Example 8 (pasty dentifrice)

| | |
|---|---|
| Sodium metaphosphate | 45.0 parts |
| Polysaccharide (A) (the product in a sucrose culture medium, average molecular weight about 200,000) | 1.0 part |
| Glycerol | 10.0 parts |
| Sorbitol | 10.0 parts |
| Water | 30.86 parts |
| Sodium laurylsulfate | 1.5 parts |
| Sodium saccharate | 0.1 part |
| Flavor | 1.0 part |
| Fungicide | 0.04 part |

In accordance wtih the above formulation, a pasty dentifrice was prepared in the same way as in Example 1.

Example 9 (transparent pasty dentifrice)

| | |
|---|---|
| Anhydrous silicon dioxide (Silicic anhydride) | 19.0 parts |
| Polysaccharide (A) (the product in a glucose culture medium, average molecular weight about 250,000) | 1.0 part |
| Glycerol | 20.0 part |
| Sorbitol | 48.0 part |
| Water | 9.35 parts |
| Sodium laurylsulfate | 1.5 parts |
| Sodium saccharate | 0.1 part |
| Flavor | 1.0 part |
| Fungicide and coloring material | 0.05 part |

In accordance with the above formulation, a pasty dentifrice was prepared in the same way as in Example 1.

Example 10 ("salt-containing" pasty dentifrice)

| | |
|---|---|
| Calcium carbonate | 40.0 parts |
| Polysaccharide (A) (the product in a glucose culture medium, average molecular weight about 100,000) | 1.0 part |
| Glycerol | 13.0 parts |
| Sorbitol | 6.0 parts |
| Water | 26.36 parts |
| Sodium laurylsulfate | 2.5 parts |
| Sodium saccharide | 0.1 part |
| Flavor | 1.0 part |
| Fungicide | 0.04 part |
| Sodium chloride | 10.0 parts |

In acordance with the above formulation, a pasty dentifrice was prepared in the same way as in Example 1.

The viscosity characteristics of the dentifrices obtained in Examples 1 to 5 were compared with those of dentifrices obtained in the same manner as in Examples 1 to 5 except that the polysaccharide was replaced by the same amount of carboxymethyl cellulose (to be referred to as Comparative Examples, 3, 4, 5, 6 and 7 corresponding to Examples 1, 2, 3, 4 and 5).

The comparison of the viscosity characteristics was performed by determining the residual amount when the dentifrice was placed in a plastic bottle (with regard to Examples 1 to 3 and Comparative Examples 3 to 5). With regard to Examples 4 and 5 and Comparative Examples 6 and 7, the viscosity characteristics was expressed by the number of pushings of a pump required to extrude the dentifrice from a pump-type receptacle.

The results are shown in Tables 3 and 4.

Table 3

| | Viscosity (poises) | Residual amount (g) |
|---|---|---|
| Example 1 | 450 | 19.0 |
| Example 2 | 460 | 10.0 |
| Example 3 | 470 | 20.0 |
| Comparative Example 3 | 440 | 35 |
| Comparative Example 4 | 450 | 18 |
| Comparative Example 5 | 440 | 35 |

It can be seen from the comparison of the residual amounts that the dentifrices of the present invention have very superior flow characteristics and viscosity characteristics. In particular, the dentifrice obtained in Example 2 using both the polysaccharide (A) and the polysaccharide (B) had very superior shape-retention and elasticity, which is indicative of the superior effect of conjointly using the polysaccharides (A) and (B).

Table 4

| Samples | Viscosity (poises) | Number of pump pushings |
|---|---|---|
| Example 4 | 380 | 6 |
| Example 5 | 370 | 6 |
| Comparative Example 6 | 370 | 16 |
| Comparative Example 7 | 380 | 26 |

The pump-type receptacle is a receptacle wherein a cylinder in a casing is moved up and down in the same principle as a pump for drawing up water from a well, thereby to reduce the pressure inside the pump, and the contents of the receptacle are drawn up by the difference in pressure between the atmospheric pressure and the pressure inside the cylinder casing. If the contents are drawn up by pushing the pump a fewer number of times, the contents have better flow characteristics in the receptacle or small openings. This means that the paste flows by a slight difference in pressure (external force). In a final form of dentifrice ready for sale, the contents can be extruded more easily when the number of pushings of the pump is smaller.

It can be seen that the dentifrices containing the polysaccharide in accordance with this invention exhibit very characteristic viscosity properties even when the viscosities are almost the same as those of the corresponding comparisons such as the dentifrice containing carboxymethylcellulose.

In the case of the comparative dentifrices, the contents can be extruded by increasing the number of pushings of the pump, but the way of extrusion was very unsatisfactory. This is in clear contrast to the Examples in which the contents could be smoothly extruded.

Then the same dentifrices as those obtained in Examples 1 to 5 and Comparative Examples 3 to 7 were filled in 10 aluminum tubes respectively, and the storage stability of the paste was examined.

The results are shown in Table 5.

Table 5

| | 50°C. to 60°C. 2 months | 50°C. to 60°C. 4 months | Room temperature 2 years |
|---|---|---|---|
| Example 1 | 0 | 0 | 0 |
| Example 2 | 0 | 0 | 0 |
| Example 3 | 0 | 0 | 0 |
| Example 4 | 0 | 0 | 0 |
| Example 5 | 0 | 0 | 0 |
| Comparative Example 3 | + | ++ | + |
| Comparative Example 4 | 0 | 0 to + | 0 |
| Comparative Example 5 | + | ++ | + |
| Comparative Example 6 | 0 to + | + to ++ | + |
| Comparative Example 7 | ++ | +++ | ++ |

0 : No separation at all
+ : The liquid component adheres thinly on the surface of the paste.
++ : Intermediate between + and +++
+++ : The liquid component and the powder component are completely separated from each other.

After storing under the conditions as given in Table 5, the paste was squeezed out, and the condition of the paste was evaluated on the following scale. The standard of evaluation was the degree of separation between the liquid component and the powder component in the composition.

If the evaluation is + or better, there is no serious problem in the dentifrice as an article of commerce. However, if the evaluation is ++ or worse, the dentifrice has poor commercial value.

It is seen from the results shown in Table 5 that the dentifrice compositions in accordance with the present invention have a far better effect of inhibiting the separation of the liquid component to the powdery component than dentifrices of conventional formulations.

What is claimed is:

1. In a liquid or pasty dentifrice, the improvement which comprises uniformly incorporating therein, a first polysaccharide having a number average molecular weight of not less than 100,000, the molecule of said first polysaccharide containing D-glucose, D-mannose, D-galactose and succinic acid in the approximate molar ratio of 1:0.03:0.1:0.2, in an amount of 0.3 to 2 parts by weight per 100 parts by weight of said liquid or pasty dentifrice.

2. The dentifrice of claim 1 including a second polysaccharide having a number average molecular weight of not less than 100,000, the molecule of which contains D-glucose, D-mannose, D-galactose and D-glucuronic acid and the approximate molar ratio of 3:2:1:2, in an amount of not more than 80% by weight based on the total amount of said first polysaccharide.

3. A liquid dentifrice which essentially consists of:

25 to 45% by weight of water, 20 to 35% by weight of abrasives, selected from the group consisting of dicalcium phosphate dihydrate, calcium pyrophosphate, anhydrous dicalcium phosphate, insoluble sodium metaphosphate, hydrated alumina, calcium carbonate, magnesium carbonate, magnesium oxide, and finely powdered silica, 20 to 35% by weight of humectants, selected from the group consisting of glycerol, sorbitol, maltitol, glucose, propylene glycol, polyethylene glycol and sodium pyrrolidone carboxylate, 0.5 to 2% by weight of detergents and surface active agents, selected from the group consisting of sodium lauryl sulfate, sodium N-lauroyl sarcosinate, α-olefin sulfonate, sodium 2-hydroxyalkyl sulfate, sodium laurylether sulfate, sodium coconut monoglyceride sulfate, sodium coconut monoglyceride sulfonate, a sodium salt of a monoester of lauroylethanolamide sulfosuccinic acid, polyoxyethylene fatty acid esters such as polyoxyethylene sorbitan monolaurate, polyoxyethylene sorbitan monopalmitate, polyoxyethylene sorbitan monostearate, polyoxyethylene stearate having a degree of polymerization of at least 25, and a polyoxyethylene polyoxypropylene block copolymer, and 0.3 to 2% by weight of a first polysaccharide having a number average molecular weight of not less than 100,000 and the molecule of said first polysaccharide containing D-glucose, D-mannose, D-galactose and succinic acid in the approximate molar ratio of 1:0.03:0.1:0.2 whereby said dentifrice has high solubility, high water-hold capacity, self-shape maintaining properties and viscoelastic properties upon removal of external pressure.

4. The dentifrice of claim 3 including a second polysaccharide having a number average molecular weight of not less than 100,000, the molecule of which contains D-glucose, D-mannose, D-galactose and D-glucuronic acid and the approximate molar ratio of 3:2:1:2, in an amount of not more than 80% by weight based on the total amount of said first polysaccharide.

5. A pasty dentifrice which essentially consists of:

25 to 35% by weight of water, 35 to 50% by weight of abrasives, selected from the group consisting of dicalcium phosphate dihydrate, calcium pyrophosphate, anhydrous dicalcium phosphate, insoluble sodium metaphosphate, hydrated alumina, calcium carbonate, magnesium carbonate, magnesium oxide, and finely powdered silica, 15 to 30% by weight of humectants, selected from the group consisting of glycerol, sorbitol, maltitol, glucose, propylene glycol, polyethylene glycol and sodium pyrrolidone carboxylate, 0.5 to 2% by weight of detergents and surface active agents, selected from the group consisting of sodium lauryl sulfate, sodium N-lauroyl sarcosinate, α-olefin sulfonate, sodium 2-hydroxyalkyl sulfate, sodium laurylether sulfate, sodium coconut monoglyceride sulfate, sodium coconut monoglyceride sulfonate, a sodium salt of a monoester of lauroylethanolamide sulfosuccinic acid, polyoxyethylene fatty acid esters such as polyoxyethylene soribitan monolaurate, polyoxyethylene sorbitan monopalmitate, polyoxyethylene sorbitan monostearate, polyoxyethylene stearate having a degree of polymerization of at least 25, and a polyoxyethylene polyoxypropylene block copolymer, and 0.3 to 2% by weight of a first polysaccharide having a number average molecular weight of not less than 100,000 and the molecule of said first polysaccharide containing D-glucose, D-mannose, D-galactose and succinic acid in the approximate molar ratio of 1:0.03:0.1:0.2 whereby said dentifrice has high solubility, high water-hold capacity, self-shape maintaining properties and viscoelastic properties upon removal of external pressure.

6. The dentifrice of claim 5 including a second polysaccharide having a number average molecular weight of not less than 100,000, the molecule of which contains D-glucose, D-mannose, D-galactose and D-glucuronic acid and the approximate molar ratio of 3:2:1:2, in an amount of not more than 80% by weight based on the total amount of said first polysaccharide.

* * * * *

UNITED STATES PATENT OFFICE
CERTIFICATE OF CORRECTION

Patent No. 3,935,307      Dated January 27, 1976

Inventor(s) Kenji Aimoto et al.

It is certified that error appears in the above-identified patent and that said Letters Patent are hereby corrected as shown below:

Item 73, line 1, delete "Sunstor", insert -- Sunstar --

Item 73, line 2, delete "Dentrificy", insert -- Dentifrice --

Item 73, line 2, before "both" insert -- Osaka-fu; --

Signed and Sealed this twenty-seventh Day of April 1976

[SEAL]

Attest:

RUTH C. MASON
Attesting Officer

C. MARSHALL DANN
Commissioner of Patents and Trademarks